US00PP12905P2

(12) United States Plant Patent
Mikaelian

(10) Patent No.: US PP12,905 P2
(45) Date of Patent: Sep. 3, 2002

(54) NECTARINE TREE NAMED 'MIKE'S RED'

(76) Inventor: Mike Mikaelian, 10368 Avenue 400, Dinuba, CA (US) 93618

( * ) Notice: Subject to any disclaimer, the term of this patent is extended or adjusted under 35 U.S.C. 154(b) by 110 days.

(21) Appl. No.: 09/639,606

(22) Filed: Aug. 15, 2000

(51) Int. Cl.[7] ..... A01H 5/00
(52) U.S. Cl. ..... Plt./190
(58) Field of Search ..... Plt./190

(56) References Cited

U.S. PATENT DOCUMENTS

PP6,363 P 11/1988 Bradford et al.

*Primary Examiner*—Bruce R. Campell
*Assistant Examiner*—Susan B. McCormick
(74) *Attorney, Agent, or Firm*—Mark D. Miller

(57) ABSTRACT

A new and distinct variety of nectarine tree is characterized by producing a semi clingstone fruit with a gold red blush coloration and is ripe for commercial harvesting and shipment August 15–20 in the San Joaquin Valley of Central California. The new variety is closely similar to the 'August Red' nectarine tree (U.S. Plant Pat. No. 6,363) from which it is a sport but from which it is distinguishable in that the fruit ripens about three to five days prior to the 'August Red' nectarine tree and the fruit is somewhat larger in size than that of the 'August Red' nectarine tree. The fruit of the in instant variety has a very good flavor compared to the 'August Red' nectarine tree.

1 Drawing Sheet

BACKGROUND OF THE NEW VARIETY

The present invention relates to a new and distinct variety of nectarine tree which will hereinafter be denominated varietally as the 'Mike's Red' nectarine tree and more particularly as a nectarine tree which produces semi clingstone fruit which can mature for commercial harvest approximately August 15–20, three to five days before 'August Red,' in the San Joaquin Valley of Central California. The fruit is a fresh market nectarine with very good red blush in coloration and larger fruit than the parent 'August Red.'

In the development of new commercial varieties of fruit trees a premium (good to excellent character) is frequently placed on those varieties that possess good size, good skin color, good flavor, as well as good holding or storage capabilities, as well as niche or specific time unique for this fruit. Thus in many instances some of the later varieties may lack one of these characteristics and would not be acceptable in the fresh market. The nectarine tree of this subject invention appear to be a promising candidate since it does not appear to have any of the above described flaws.

ORIGIN AND ASEXUAL REPRODUCTION OF THE NEW VARIETY

The present variety of nectarine tree was discovered by the inventor in his orchard of 'August Red' nectarine trees (U.S. Plant Pat. No. 6,363) which is located near Cutler, Calif. in the San Joaquin Valley of Central California. The inventor discovered the new variety as a sport of the 'August Red' nectarine tree in 1996. The new variety was first asexually reproduced by the inventor's representative in 1998–1999 by bud grafting trees in a nursery in Fowler, Calif. on Nemared rootstock using buds from mature wood. The asexually reproduced trees first bore fruit of the new variety in August 2000. The inventor carefully compared the asexually reproduced trees with the parent including the fruit thereof and has confirmed that the parent's progeny are in all respects identical.

SUMMARY OF THE NEW VARIETY

The 'Mike's Red' nectarine is characterized by producing a semi clingstone fruit which has a good red blush coloration and is ripe for commercial harvesting and shipment approximately August 15–20 in the San Joaquin Valley of Central California. The new variety is closely similar to the 'August Red' nectarine tree (U.S. Plant Pat. No. 6,363) but from which it is distinguishable in that it ripens three to five days earlier than the fruit of the 'August Red' nectarine tree and the fruit is somewhat larger in size than that of the 'August Red' nectarine tree. The fruit of the new variety produces a very good flavor.

BRIEF DESCRIPTION OF THE DRAWING

The accompanying drawing is a color photograph showing fruit of the new variety including, starting on the right side, a bottom view showing the apex and suture thereof, a second view showing the top with stem cavity thereof, a third view showing a side view with the cheek surface thereof, a fourth view of the shape of the apical and basal ends of the fruit, a fifth view sectioned to show the flesh thereof and the pit cavity, the pit (or stone), and the last view of the foliage typical of the new variety of nectarine tree.

DETAILED DESCRIPTION

Referring more specifically to the pomological details of this new and distinct variety of nectarine tree, the following has been observed under the ecological conditions prevailing at the orchard of origin which is located near Cutler, Calif. in the San Joaquin Valley of Central California. All major color designations are by reference to the Dictionary of Color by Maerz & Paul, First Edition 1930. Common colors are also commonly employed.

TREE

Generally, amount of top growth is about equivalent to that produced by the parent tree 'August Red.'

Vigor: Good.
Figure: Upright and slightly spreading.
Productivity: Very good.
Regularity of bearing: Regularly under typical ecological conditions for the Central California San Joaquin Valley.
Trunk:
*Size.*—Medium to large — 39 inches in circumference as measured 10 inches above soil level.
*Age.*—Tree is 12 years old.
*Surface texture.*—Moderately rough.
*Color code.*—Pigeon (55-A-3).
*Lenticels.*—Numbers — moderate. Size — medium. Length — 1–2 mm (0.04–0.079 inch). Color — Turtle Dove (55-C-1).
Branch:
*Size.*—Medium to large. Circumference — 12 inches, Measurements taken about 2 feet above soil level. Texture: Mature branches, slightly rough. Immature branches, smooth.
*Color code.*—One year or older, Haematite Red (7-H/J-3).
*Color code.*—Immature, Ferns (21-I-7).
Leaves:
*Size.*—Large. Length — 147–158 mm (5.79–6.22 inch). Width — 48–56 mm (1.89–2.20 inch). Form —Lanceloate, leaf tip is acuminate. Color code: Upwardly disposed surface — Civette (22-E-8). Downwardly disposed surface — Chromium Ox Opaq F (21-B-8). Marginal Form crenate.
Leaf vein:
*Color code.*—Russet Green (20-K-1).
*Thickness.*—1½ mm (0.059 inch).
Petiole:
*Size.*—Medium to long.
*Length.*—13–15 mm (0.51–0.59 inch).
*Thickness.*—1½–2 mm (0.059–0.078 inch).
*Color code.*—Russet Green (20-K-1).
Glands:
*Size.*—Medium — two.
*Width.*—Small — less than 1 mm (0.04 inch).
*Length.*—Up to 1 mm (0.04 inch).
*Position.*—Alternate at base at leaf.
*Form.*—Reniform. Yellow-green — greenish brown (30-A-1).
Stipule: Small in size 3 mm (0.12 inch), doubled — reddish brown (7-L-2).

FLOWERS

Flower buds:
*Size.*—Dormant flower buds — medium to large. Length — 10 mm (0.39 inch). Width — 8 mm (0.32 inch).
*Length.*—Medium.
*Form.*—Conic and closely attached to the fruit wood — slightly Pubescent.
*Bud scales.*—Color — brownish red (6-L-10).
Flower: Generally showy.
*Diameter.*—Large at full bloom, 33 mm (1.30 inch) to 39 mm (1.54 inch).
*Date of bloom.*—Approx. 80% of full bloom Feb. 24, 2000; 100% of full bloom by Feb. 29, 2000.
*Bloom quality.*—Abundant.
*Pollen.*—Present — self fertile.
*Petal size.*—Large, five in number. Length — 14 mm (0.55 inch) to 16 mm (0.63 inch). Width — 11 mm (0.43 inch) to 13 mm (0.51 inch). Color — Light Pink (1-H-2).
*Fragrance.*—Slight.
*Petal claw.*—Broadly truncate. Width — 1.5 mm (0.059 inch). Length — 1–2 mm (0.04 to 0.079 inch).
*Petal margin.*—Moderately indulate with a generally rounded apex.
*Flower pedicel.*—Length — short — avg. 2 mm (0.079 inch). Thickness — avg. 2 mm (0.079 inch). Width — 1.5 mm (0.059 inch). Color —Russet Green (20-K-1).
*Calyx.*—Color — green at base (18-K-4) and maroon near base and sepals (7-H-6). Surface — glabrous.
*Sepals.*—Medium to large, surface pubescent, moderately ovate — peony, color Burmese Ruby (7-H-6).

FRUIT

Maturity: Aug. 18–23.
Size:
*Average diameter in axial plane.*—72–80 mm (2.83–3.15 inches).
*Average in transverse in suture plane.*—68–74 mm (2.67–2.9 inches).
*Average in transverse at right axis to suture plane.*—65–69 mm (2.56–2.72 inches).
Form:
*Uniformity.*—Uniform.
*Symmetrical or asymmetrical.*—Slightly Asymmetrical.
*Suture.*—Pronounced but not deep.
*Ventral surface.*—Slightly uneven.
*Stem cavity.*—Relatively shallow. Width — 15–19 mm (0.59–0.75 inch). Depth — 5–7 mm (0.20–0.28 inch). Length — 15–20 mm (0.59–0.79 inch). Shape —generally ovate.
Stem: Generally short.
*Length.*—5–7 mm (0.20–0.28 inch).
*Caliper.*—2–4 mm (0.08–0.16 inch).
Apex: Round.
Pistal point: Retuse.
Base: Rounded.
Skin:
*Thickness.*—Normal for nectarine.
*Texture.*—Firm and smooth.
*Tendency to crack.*—Not known.
*Color code.*—Blush color — Chianti, Antique (6-L-6) —Over half to ⅔ of fruit. Ground color — Rattan (11-K-5).
*Flesh color.*—Near the skin, Pearl Blush (12-A-5). Near the pit well — reddening Rubient (55-L-8).
*Color of surface of pit cavity.*—Rubient (55-L-8).
*Color of pit well.*—Phlox (54-H-12).
Juice production: Good.
Flavor: Very good — sweet.
Aroma: Good.
Texture: Firm.
Fibers:
*Numbers.*—Many.
*Texture.*—Stringy.
Ripening: Even.
Eating quality: Good.

Average pressure test in this orchard of parent tree was 11.8 in 1999, and average brix was 10.8. These figures will vary according to size and number on the tree along with climatic factors during maturing as well as cultivate practices.

STONE

Free or cling: Semi clingstone.
Fibers: Adhering to stone.
*Numbers.*—Many.
*Length.*—Long — 15 mm (0.59 inch).
Size:
*Length.*—34 mm (1.34 inch).
*Width.*—27½ mm (1.08 inch).
*Thickness.*—13–15 mm (0.51–0.59 inch).
Form: Generally ovate.
Apex shape: Rounded with blunt point.
Color dry: Raisin-Rubient (55-J/L-8).
Base: Slightly flattened.
Sides: Generally unequal.
Hilum: Scar is small, oval in shape.
Ridges: Grooved with ventral edge, relatively narrow — tight groove from base to base to apex.
Tendency to split: Not known.
Use: Fresh market.

The present nectarine tree is raised in the San Joaquin Valley of Central California where it is dormant during the winter, so winter hardiness is not a problem. Since the invention is normally irrigated during the growing season, drought is not a factor. There does not appear to be any evidence of heat susceptibility for the fruit as well as the foliage. Although the new variety of nectarine trees possesses the above described characteristics as a result of the growing conditions prevailing near Cutler, Calif. in the Central San Joaquin Valley, it is to be understood that variations of the usual magnitude and characteristics may occur as a result of changes in growing conditions, irrigation, fertilization, pruning, pest control, climatic variations and the like are to be expected.

Having thus described and illustrated my new variety of nectarine tree which I claim as new and desire to be secured by plant letters patent is:

1. A new and distinct variety of nectarine tree substantially as illustrated and described which is remotely similar to 'August Red' nectarine tree (U.S. Plant Pat. No. 6,363) from which it is a sport by producing an earlier maturing fruit with good size and good exterior coloration and eating quality which are mature for commercial harvesting and shipment approximately August 15–20 or about three to five days earlier than the fruit of 'August Red'.

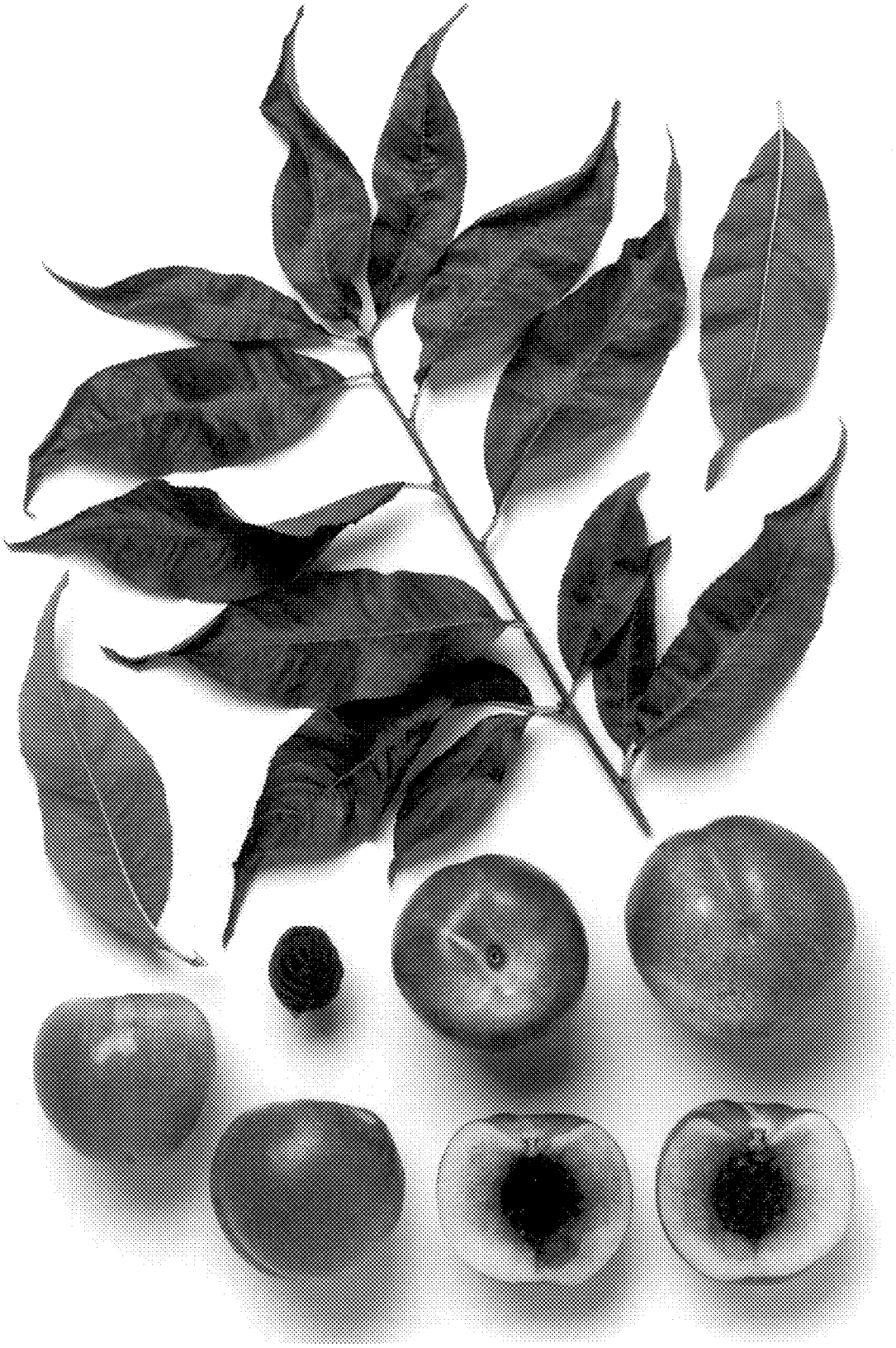

* * * * *